United States Patent [19]

Martin

[11] Patent Number: 5,254,591
[45] Date of Patent: Oct. 19, 1993

[54] PHARMACEUTICAL COMPOSITION FOR TREATING GASTROESOPHAGEAL REFLUX

[75] Inventor: Christopher J. Martin, Victoria, Australia

[73] Assignee: The University of Melbourne, Parkville, Australia

[21] Appl. No.: 867,065

[22] Filed: Apr. 10, 1992

Related U.S. Application Data

[63] Continuation of Ser. No. 737,392, Jul. 29, 1991, abandoned, which is a continuation of Ser. No. 370,111, Jun. 21, 1989, Pat. No. 5,036,057, which is a continuation of Ser. No. 127,662, Dec. 21, 1987, abandoned.

[30] Foreign Application Priority Data

Jan. 3, 1986 [AU] Australia .................... PH4084

[51] Int. Cl.$^5$ .................. A61K 31/16; A61K 47/00
[52] U.S. Cl. ..................... 514/616; 514/779; 514/54; 514/304; 514/312; 514/535; 514/626; 514/654; 424/687
[58] Field of Search ............... 424/156; 514/54, 304, 514/312, 535, 626, 654, 616, 779

[56] References Cited

U.S. PATENT DOCUMENTS

4,140,760  2/1979  Withington .................. 424/156

OTHER PUBLICATIONS

Handbook of Nonprescription Drugs 5th ed., Amer. Pharm. Assoc., Washington, D.C. 1977 pp. 9–10.
Physician's Desk Reference 22nd ed. 1968 p. 1235.

*Primary Examiner*—S. J. Friedman
*Assistant Examiner*—William Jarvis
*Attorney, Agent, or Firm*—Dilworth & Barrese

[57] ABSTRACT

A pharmaceutical composition useful for treating gastroesophageal reflux comprising oxethazaine and a carrier selected from alginic acid and alginates.

5 Claims, No Drawings

PHARMACEUTICAL COMPOSITION FOR TREATING GASTROESOPHAGEAL REFLUX

This is a continuation of copending application Ser. No. 07/737,392 filed on Jul. 29, 1991, now abandoned which is a continuation of Ser. No. 07/370,111 filed on Jun. 21, 1989 now U.S. Pat. No. 5,036,057 which is a continuation of Ser. No. 07/127,662 filed on Dec. 21, 1987, now abandoned.

This invention relates to reflux.

In a particular aspect this invention relates to gastroesophageal reflux (commonly known as "heartburn").

In some humans, the lower esophageal sphincter is prone to relaxing more frequently than in other humans. As a consequence gastrointestinal fluid can pass into the esophagus at such times as the lower esophageal sphincter is relaxed so causing the burning pain more commonly known as "heartburn".

Our research has shown that if a local anaesthetic is applied to gastric mucosa below the lower esophageal sphincter the frequency of relaxation can be materially reduced.

However, a major delivery problem is to obtain contact of the local anaesthetic with the gastric mucosa below the lower esophageal sphincter.

In this last respect, methods of delivery in which a local anaesthetic is dissolved or otherwise at least substantially uniformly distributed in gastrointestinal fluids have not been satisfactory as unacceptably high dosages of local anaesthetic would be necessary.

The present invention provides a pharmaceutical composition comprising a local anaesthetic adapted to inhibit relaxation of the lower esophageal sphincter and a carrier therefor comprising a material adapted to float on gastrointestinal fluids contained in the stomach whereby to be more proximate to the gastric mucosa below said sphincter, than said fluids. Said carrier preferably includes a foam or a material adapted to form a foam in the presence of gastrointestinal fluids.

Said carrier may include a material adapted to form a foam cell wall and a blowing agent.

Suitable materials for forming foam cell walls include alginic acid and alginates and surface active agents.

Suitable blowing agents include those capable of being decomposed by gastrointestinal fluids to produce carbon dioxide.

A suitable carrier is Gaviscon produced by Reckitt & Coleman. This carrier is described in U.S. Pat. No. 4,140,780 and the whole of the subject matter thereof is incorporated hereto.

Said carrier may alternatively comprise a mucilage and a low density liquid adapted together to form a mucilage gel in the human stomach.

Another carrier is described in GB Patent Specification No. 2,008,408 and the whole of the subject matter thereof is incorporated hereinto.

Said carrier may be in the form of a liquid or solid.

The local anaesthetic may be any suitable anaesthetic but amongst them cocaine, oxethazine and benzocaine appear to be most effective. Suitable other alternatives include amethocaine, cinchocaine and lignocaine.

The present invention will be further illustrated by the following Example and the following Tests and Discussion.

EXAMPLE 1

40 mgm of oxethazine was blended with 2,000 mgm Gaviscon and tabletted to form a dosage unit.

Gaviscon is a proprietary material produced by Reckitt & Coleman and containing $NaHCO_3$, $Al(OH)_3$, $Mg_2Si_3O_8$ and alginic acid. In gastrointestinal fluids the $NaHCO_3$ is decomposed to produce $CO_2$ which with the alginic acid or an alginate formed therefrom produces a foam which floats the mixture on top of gastrointestinal fluids.

EXAMPLE 2

100 mgm of cocaine was blended with 2,000 mgm Gaviscon and tabletted to form a dosage unit.

EXAMPLE 3

Granules were prepared from a mixture containing in proportions by weight:
1,000 alginic acid
50 magnesium trisilicate
200 aluminium hydroxide
380 sodium bicarbonate
40 oxethazine
3,000 sucrose

EXAMPLE 4

Tablets were prepared from a mixture containing in proportions by weight:
500 alginic acid
25 aluminium hydroxide
170 sodium bicarbonate
10 cocaine
640 sucrose

EXAMPLE 5

A liquid composition was prepared and contained in proportions by weight:
1,000 sodium alginate
320 calcium carbonate
530 sodium bicarbonate
500 water

TEST 1

In humans and dogs most episodes of gastro-esophageal reflux of gas and liquid occur as a result of distinctive, transient lower esophageal sphincter relaxations (TLOSRs) which last from 3-35 seconds. In studies in 4 trained unsedated dogs we have examined the hypothesis that upper gastric sensory receptors trigger TLOSRs. A manometric sleeve side hole catheter, passed via a cervical esophagostamy, monitored esophageal motor function. The rates of occurrence of TLOSRs stimulated by gastric insufflation or air, 80 ml/min, were determined initially for 1 hour and then for a second hour after treatment of a 5 cm ring of gastric mucosa around the esophageal opening with either 20 ml water or 20 ml of 1% cocaine solution, sprayed per-endoscopically via a gastric cannulum.

The cocaine treatment described above was associated with significant ($F=3.41$, $p<0.05$) reduction of TLOSR rate (see Table).

TABLE

| TIME TREATMENT | 1st Hour Cocaine | 2nd Hour Water | 1st Hour Water | 2nd Hour Water |
|---|---|---|---|---|
| TLDSR RATE | 8.6 | 3.5 | 6.8 | 7.0 |

There was no detectable effect on TLOSR rate from application of cocaine 1%, either to the lowermost 5 cm of esophageal mucosa (5 ml) or to a 1 cm ring of gastric mucosa around the esophageal opening (0.8-5 ml). Cocainization of the esophageal mucosa did however block primary and secondary peristalsis of the distal esophagus.

The inhibition of TLOSR rate by topical cocaine is more consistent with blockade of mucosal or deeper gastric sensory receptors than a central nervous action. This inhibition supports the concept that TLOSRs are triggered by gastric sensory receptors.

DISCUSSION

The traditional concept is that gastro-esophageal reflux occurs across a feeble lower esophageal sphincter because of pressure differentials between stomach and esophagus. Until 1976 it was not possible to achieve prolonged measurement of lower esophageal sphincter pressure except in animals sedated by general anasthesia because of continual movement of the lower esophageal sphincter, and consequently continual movement of side holes in relation to the point of maximal pressure in that sphincter: general anasthesia itself abolishes TLOSRs. This problem was successfully overcome by development of the sleeve sensor device (Dent 1976) which is now commonly termed the Dent sleeve. By use of this sleeve it was subsequently demonstrated that the majority of gastro-esophageal reflux episodes in man occurred after periods of complete transient lower esophageal sphincter relaxation (TLOSRs). Such relaxations occurred most often without any prior pharyngeal or esophageal body motor event, and were distinct from the normal swallow-induced LOS relaxation (Dent et al. 1980). The relaxation had an abrupt onset and usually lasted from 5 to 35 seconds. That time pattern was thought to be suggestive of a neural mediation. Subsequent to those initial studies on normal man (Dodds et al., 1982), demonstrated that the most common mechanism of gastro-esophageal reflux in patients with peptic esophagitis was also the TLOSR.

Other studies on TLOSRs in man have added to the understanding of this important phenomenon. Gastric gaseous distension has been shown to be a potent trigger of TLOSRs in normal subjects. Venting of gas from the stomach occurs only during TLOSRs and these appear to be under control of mechanisms which sense gastric distension. This phenomenon is suppressed by change from the erect to the supine posture—possibly indicating that there is overriding control of TLOSRs from higher centres, acting to limit acid reflux in the supine position, where venting of gas is likely to result in concomitant acid reflux due to the close proximity of acid to the LOS in that position. These data have confirmed that TLOSRs in man are at least in part triggered by gastric distension. It is relevant to the pursuit of the study of TLOSRs that gastric distension as occurs postprandially is a well-known and potent trigger of reflux in patients with pathological gastro-esophageal reflux.

On the basis of the observations summarised above, it appears that the TLOSR is a normal physiological response which allows venting of the stomach. It follows therefore, that pathological gastro-esophageal reflux results from defective control of this lower esophageal sphincter response. The following hypotheses have been constructed by us about normal control of TLOSRs:

1. Gastric stretch receptors are an important trigger of TLOSRs and afferent fibres from these receptors travel up the vagus to the hind brain, or possibly by local intramural pathways to the lower esophageal sphincter;
2. Signals from afferent fibres are integrated either in the CNS or in the myanteric plexus and lead to stimulation of non-cholinorgic, non-adronorgic neural elements which inhibit the lower esophageal sphincter;
3. TLOSRs are suppressed by inputs from other sensory receptors (e.g. gastric mucosal and receptors which sense posture). The concepts of triggering and control of TLOSRs contained in the hypotheses stated above suggest the possibility of new approaches to the management of pathological gastro-esophageal reflux. Current surgical methods for treatment of gastro-esophageal reflux depend on fashioning of a mechanical substitute for the lower esophageal sphincter, an approach which has significant morbidity and failure rate, particularly in the hands of surgeons who perform anti-reflux surgery infrequently. Definition of sensory and motor neural pathways that produce TLOSRs may allow adjustment of the threshold for the production of relaxations by selective nerve sectioning, an approach which may prove more durable, less morbid and technically simpler than current anti-reflux operations. Identification of the pharmacological mechanisms responsible for TLOSRs would allow a specification of the type of pharmacological agent which would need to be developed to treat disordered gastro-esophageal incompetence effectively.

Ethical constraints make it impossible to pursue rigorously in man the hypotheses stated above. Accordingly, we worked on establishing a method to identify and subsequently characterise TLOSRs in animals. Because TLOSRs do not occur during stable sleep in man, nor during anaesthesia in animals, we chose to study the unsedated trained dog. Esophageal motor function was studied with manometric methods based on those used for the initial studies of TLOSRs in man (Dent et al. 1980: Dodds et al. 1982). A manometric sleeve catheter assembly, passed via a Komarov cervical esophagostomy, monitored gastric, lower esophageal sphincter, and esophageal body pressures. A separate catheter was passed orad into the pharynx to monitor swallowing. A miniature glass pH electrode was positioned 5 cm. above the lower esophageal sphincter. Thus equipped, it proved possible to monitor motility and occurrence of reflux episodes for several hours, during fasting and after food. These studies have demonstrated that gastro-esophageal reflux occurs during TLOSRs in dogs as well as in man. As with man the reflux producing LOS relaxation in the dog was usually unrelated to swallowing.

Spontaneous gastro-esophageal episodes and TLOSRs occurred infrequently in our dogs (less than 1/hour). In order to study the mechanisms and control of TLOSRs, it was necessary to devise a stimulus which would trigger these relaxations at a higher frequency. Experience in man suggested that gastric gaseous distension would be effective for this purpose in dogs. This has proved to be the case. Continuous gastric insufflation with air at a rate of 80 ml./min. resulted in stimulation of 10.3 TLOSRs/hour. These TLOSRs were associated with audible belching and were identical to those associated with gastro-esophageal reflux.

Using this model, we have examined the question of whether TLOSRs are mediated via vagal nerve fibres or by local intra-mural nerve pathways. For that purpose, trained dogs were prepared with cervical vago-sympathetic trunks isolated in bridges of cervical skin, so that reversible vago-sympathetic blockade could be produced by cooling. Blockade was confirmed by the development of tachycardia greater than 150/minute, slow deep respiration, failure of esophageal peristalsis in response to swallowing and bilateral Horner's syndrome. In a series of experiments esophageal manometry was performed for 30 minutes before, followed by 30 minutes during and then 30 minutes after vagal blockade. In all four dogs studied, complete vagal blockade during gastric insufflation abolished without exception TLOSRs and belching, despite reduction of lower esophageal sphincter pressure from $18.5 \pm 5.9$ mmHg, to $9.3 \pm 6.0$ mmHg (S.E.). Within one to four minutes of cessation of cooling, TLOSRs and belching returned. Administration of two doses of atropine (50 and 200 microgram/kg. iv) did not block TLOSRs or gas reflux. We interpreted these findings as follows:

1. TLOSRs are produced by neural pathways;
2. Either sensory and/or motor pathways that trigger TLOSRs travel within the vagus;
3. TLOSRs produced by gastric distension are not triggered by local intra-mural fibres that pass directly from the stomach to the lower esophageal sphincter;
4. Muscarinic mechanisms are not primarily involved in the mediation of TLOSRs. The results of these initial studies have recently been published (Martin et al, 1988).

On the basis of these experiments we proposed as a working model that TLOSRs triggered by gaseous distension arose from mechanoreceptors situated in the fundus of the stomach, travelled up afferent pathways which were probably vagal, were integrated in the hind brain, and then returned down vagal inhibitory non-cholinergic and non-adrenergic pathways to produce lower esophageal sphincter relaxation.

We have sought to study the sensory arm of this arc. We have performed selective nerve division studies of the fundus of the stomach, and we have attempted to inhibit the occurrence of transient lower esophageal sphincter relaxations pharmacologically. Of particular relevance are our pharmacological studies. We have demonstrated in the dog that transient lower esophageal sphincter relaxations produced by gastric insufflation are inhibited by topical application of local anaesthetic to the fundic mucosa.

Amongst the agents that have been tested so far are cocaine, lignocaine bupivicaine, benzocaine and oxethazaine. We were unable to demonstrate significant reductions of TLOSRs by topical application of lignocaine or bupivicaine to upper gastric mucosa. We therefore examined the effect of topical benzocaine which because of its low pKa (3.5) might be expected to be better absorbed across the gastric mucosa, a lipid membrane. An effect of similar magnitude to that observed with cocaine was recorded, however, the concentrations of benzocaine required to produce this effect were high, thereby limiting the pharmacological usefulness of this agent in humans. Some special properties of the local anaesthetic agent oxethazaine made it particularly useful in the acidic gastric environment. As a weak base it is relatively unionized in acid solution giving it the same theoretical advantageous adsorbtive properties of benzocaine. Furthermore the high fat solubility of the derivative oxethazaine HCl make penetrations of lipid membranes of the gastric mucosa and the myelin sheaths of gastric nerves by the salt derivative likely.

In paired studies suing 100 mg of oxethazaine sprayed onto the upper 5 cm area of gastric mucosa, just distal to the lower esophageal sphincter we found that by comparison with control that oxethazaine reduced the incidence of TLOSRs produced by gastric insufflation in 4 of 5 dogs. Increase of the dose applied to 400 mg, inhibited the TLOSR response in all 4 dogs tested. In further studies in 7 dogs in which 40 mg of oxethazaine was incorporated into 20 ml of liquid gaviscon and then mixed with canned meat, a 35% reduction in gastro-esophageal venting of gastric contents was observed in the 2 hour postprandial period.

Accordingly, using a pharmaceutical carrier which will result in a local anaesthetic being brought to being specifically proximate to the fundic mucosa will have significant effect in reducing TLOSRs.

The claims defining the invention are as follows:

1. A pharmaceutical composition comprising
   (i) oxethazaine in an amount sufficient to indirectly inhibit relaxation of the lower esophageal sphincter by acting on mechanoreceptors located in the fundus of the stomach, and
   (ii) a carrier for said oxethazaine selected from the group consisting of alginic acid and alginates, said carrier adapted to float on gastrointestinal fluids contained in the stomach such that said carrier is more proximate to the gastric mucosa below said sphincter than said gastrointestinal fluids, said carrier being accordingly adapted to deliver said oxethazaine to the fundic mucosa such that it is able to act on said mechanoreceptors.

2. A pharmaceutical composition as claimed in claim 1, wherein said carrier includes a foam, or a material adapted to form a foam in the presence of gastrointestinal fluids.

3. A pharmaceutical composition as claimed in claim 2, wherein said carrier is adapted to form a foam cell wall and includes a blowing agent.

4. A pharmaceutical composition as claimed in claim 3, wherein said blowing agent is one capable of being decomposed by gastrointestinal fluids to produce carbon dioxide.

5. A pharmaceutical composition as claimed in claim 1, wherein said oxethazaine is present in said composition in an amount of 1% to 10% by weight.

* * * * *